(12) United States Patent
Park

(10) Patent No.: US 8,951,231 B2
(45) Date of Patent: Feb. 10, 2015

(54) ASEPTIC ADJUSTABLE ASPIRATION CATHETER DEVICE

(75) Inventor: Jaechan Park, Daegu (KR)

(73) Assignee: Kyungpook National University Industry Academic Cooperation Foundation (KR)

( * ) Notice: Subject to any disclaimer, the term of this patent is extended or adjusted under 35 U.S.C. 154(b) by 822 days.

(21) Appl. No.: 13/054,735

(22) PCT Filed: Mar. 24, 2009

(86) PCT No.: PCT/KR2009/001499
§ 371 (c)(1),
(2), (4) Date: Mar. 8, 2011

(87) PCT Pub. No.: WO2010/008127
PCT Pub. Date: Jan. 21, 2010

(65) Prior Publication Data
US 2011/0160704 A1    Jun. 30, 2011

(30) Foreign Application Priority Data
Jul. 15, 2008  (KR) .................. 10-2008-0068621

(51) Int. Cl.
*A61M 25/16*    (2006.01)
*A61M 25/01*    (2006.01)
(Continued)

(52) U.S. Cl.
CPC ....... *A61M 25/0111* (2013.01); *A61M 25/0041* (2013.01); *A61M 39/18* (2013.01); *A61M 39/20* (2013.01); *A61M 2210/1089* (2013.01)
USPC .................... 604/171; 604/95.04; 604/165.01

(58) Field of Classification Search
CPC ..................... A61M 25/0111; A61M 25/0108; A61M 25/0147; A61M 5/16859; A61M 5/172; A61M 25/0136
USPC ............. 604/518, 528, 8, 95.04, 171, 164.01, 604/165.01, 544; 606/41
See application file for complete search history.

(56) References Cited

U.S. PATENT DOCUMENTS 4,224,951 A    9/1980  Hasson
4,327,709 A    5/1982  Hanson et al.
(Continued)

OTHER PUBLICATIONS

Insert: Merriam-Webster Dictionary. Accessed online: Jun. 6, 2014.*
(Continued)

*Primary Examiner* — Bhisma Mehta
*Assistant Examiner* — Matthew A Engel
(74) *Attorney, Agent, or Firm* — Levenfeld Pearlstein, LLC

(57) ABSTRACT

An aseptic re-aspiration catheter apparatus for removing body fluids from a human body includes a front connector connected to a guide tube, into which a catheter having a predetermined length is inserted, and an adjustment tube having a predetermined length. The leading end of the adjustment tube is assembled to the front connector. A front locking member has an inner hole into which the catheter is inserted, is detachably assembled to the front connector, and is disposed inside the adjustment tube. A rear connector is assembled to the rear end of the adjustment tube. A rear locking member is connected to the catheter and detachably assembled to the rear connector, and extends through the connectors. A cap member is detachably assembled to the rear locking member. Blood clots, abscesses, and blood fluids are simply and safely removed from the human body in a short time using the catheter.

20 Claims, 5 Drawing Sheets

(51) Int. Cl.
*A61M 25/00* (2006.01)
*A61M 39/18* (2006.01)
*A61M 39/20* (2006.01)

(56) References Cited

U.S. PATENT DOCUMENTS

| | | | | |
|---|---|---|---|---|
| 4,676,228 A | * | 6/1987 | Krasner et al. | 600/116 |
| 4,787,884 A | * | 11/1988 | Goldberg | 604/8 |
| 4,913,683 A | * | 4/1990 | Gregory | 604/8 |
| 4,950,226 A | * | 8/1990 | Barron | 604/8 |
| 5,527,292 A | * | 6/1996 | Adams et al. | 604/171 |
| 5,792,094 A | * | 8/1998 | Stevens et al. | 604/4.01 |
| 5,876,373 A | * | 3/1999 | Giba et al. | 604/95.04 |
| 6,044,845 A | * | 4/2000 | Lewis | 128/898 |
| 6,551,302 B1 | * | 4/2003 | Rosinko et al. | 604/505 |
| 6,613,014 B1 | | 9/2003 | Chi | |
| 7,691,095 B2 | * | 4/2010 | Bednarek et al. | 604/523 |

OTHER PUBLICATIONS

Into: Merriam-Webster Dictionary. Accessed online: Jun. 6, 2014.*
International Search Report for PCT/KR2009/001499, dated Nov. 9, 2009.

* cited by examiner

ASEPTIC ADJUSTABLE ASPIRATION CATHETER DEVICE

CROSS-REFERENCE TO RELATED APPLICATIONS

This is a National Stage Application of International Patent Application No. PCT/KR2009/001499, filed Mar. 24, 2009, which claims the benefit of and priority to Korean Patent Application No. 10-2008-0068621, filed Jul. 15, 2008, the contents of each of which are incorporated fully by reference herein.

TECHNICAL FIELD

The present invention relates to a catheter apparatus permitting re-aspiration and repositioning of the aspiration area after a surgical operation, and more particularly, to an aseptic re-aspiration catheter apparatus, which is improved such that the position thereof can be adjusted simply and safely without an additional sterilization or disinfection process on a bed, the clogging of a catheter can be prevented, and blood clots, abscesses, and blood fluids can be aspirated.

BACKGROUND ART

In general, a catheter apparatus is a medical tubular instrument that is used to examine a diseased area by aspirating blood, blood clots, body fluids, or the like from the human body, to inject a medicine into the body, or to expand a strictured lumen.

The catheter apparatus is classified into various types, including a urethral catheter, which is used to discharge urine, to clean the bladder, or to inject a medicine into the bladder; a balloon catheter, which is used in a surgical procedure of expanding cardiac blood vessels; a Hickman catheter, which is inserted into a vein in order to inject a medicine and collect blood; a tracheal catheter, which is used to remove impurities taken into the trachea or throat of a newborn baby, right after the delivery; a dental suction catheter, which is used to take in and discharge a blood fluid or saliva that is produced while a dental operation is underway; etc.

In the meantime, a surgical procedure using a flexible catheter apparatus made of a synthetic resin, selected from among the various types of catheter apparatus described above, involves inserting a catheter having a predetermined length into the human body, removing blood, blood clots, or body fluids from the human body by aspirating it, fixing the catheter to the operated area, and finishing the operation.

Here, if a small amount of blood that has bled remains in the cranium or abdominal cavity, it is possible to dissolve it by injecting a medicine, such as urokinase, using the catheter.

In the catheter apparatus of the related art, the catheter is fixed to the operated area. Thus, in the state in which the catheter is inserted into the body, if the aspiration passage of the catheter is clogged or the aspiration area of the catheter is required to be repositioned, a reoperation, which involves removing the existing catheter from the operated area and placing a new catheter in the operated area, is required.

The reoperation of reinstalling the catheter disadvantageously requires anesthesia, sterilization, and disinfection processes and prolongs the recovery period of the patient, thereby increasing the physical and emotional distress of the patient.

DISCLOSURE

Therefore, the present invention has been devised in order to solve the foregoing problems, and an object of the invention is to provide a catheter apparatus in which blood clots, abscesses, and blood fluids can be simply and safely removed by being discharged from the human body in a short time through aspiration using a catheter, which is installed in an initial operation, without an additional anesthesia process or additional sterilization and disinfection processes on a bed, and in which the aspiration area of the catheter can be simply and precisely repositioned.

As a specific means for realizing the foregoing object, the invention provides an aseptic re-aspiration catheter apparatus for removing body fluids from a human body. The catheter includes a front connector connected to a guide tube, into which a catheter having a predetermined length is inserted; an adjustment tube having a predetermined length, the leading end thereof being assembled to the front connector; a front locking member having an inner hole into which the catheter is inserted, the front locking member being detachably assembled to the front connector and being disposed inside the adjustment tube; a rear connector assembled to the rear end of the adjustment tube; a rear locking member, which is connected to the catheter and detachably assembled to the rear connector, and extends through the front and rear connectors, and a cap member detachably assembled to the rear locking member.

It is preferred that the catheter have a plurality of aspiration holes in the leading end thereof.

It is preferred that the guide tube have a burying portion on the leading end thereof, the burying portion inclined at a predetermined angle.

It is preferred that the catheter or the guide tube have at least one position locator made of a material that prevents radiation from passing through.

It is preferred that the front connector includes an inner tube having an inner hole such that the rear end of the guide tube and the leading end of the front locking member are inserted into the hole; an outer tube having an inner diameter greater than that of the inner tube, the outer tube being assembled to the leading end of the adjustment tube; and a partition extending from the outer surface of the inner tube such that the partition halves a space inside the outer tube.

It is more preferred that the partition have at least one pore. The pore penetrates the partition such that a space inside the adjustment tube communicates with an outside.

It is preferred that the adjustment tube be made of a material, which is transparent or semitransparent such that the inside of the adjustment tube is identifiable by eyes, and is soft such that the adjustment tube is contractible and expandable along the long axis.

It is preferred that the front end of the adjustment tube is fixed in position by a front sleeve, in which the front sleeve is inserted into the rear end of the front connector, and the rear end of the adjustment tube is fixed in position by a rear sleeve, in which the rear sleeve is inserted into the front end of the rear connector.

It is preferred that the front locking member include a front body having a front inner hole into which the catheter is inserted and fitted, with part of the leading end of the front body being inserted into an inner hole of the front connector, and a rear body extending from the front body. The rear body has a rear inner hole through which the catheter extends, and the leading end of the rear body is in contact with the front connector.

It is more preferred that the front inner hole have an inner diameter equal with or smaller than the outer diameter of the catheter, and the rear inner hole have an inner diameter greater than the outer diameter of the catheter.

It is more preferred that the front body have at least one slit in the leading end thereof, the leading end having a cross section such that the outer diameter thereof increases in the direction toward the rear body.

It is more preferred that the size of the rear body be greater than the inner diameter of the outer tube, which is provided on the rear end of the front connector, and smaller than the outer diameter of the outer tube.

It is more preferred that the rear body have a plurality protrusions formed on the outer surface thereof.

It is more preferred that the rear body have a cross section such that the outer diameter of the central portion thereof is relatively smaller than those of opposite ends thereof.

It is preferred that the rear connector include an inner tube having a predetermined size through which the catheter is moved forward and backward by being inserted thereinto, an outer tube having an inner diameter relatively greater than the inner tube, the outer tube assembled to the rear end of the adjustment tube, and a partition extending from the outer surface of the inner tube to half the space inside the outer tube.

It is more preferred that the partition have at least one pore, the pore penetrating the partition such that the space inside the adjustment tube communicates with the outside.

It is more preferred that the inner hole include a large diameter portion spaced apart from the outer surface of the catheter, the large diameter portion having an inner diameter relatively greater than the outer diameter of the catheter, and a small diameter portion contacting the outer surface of the catheter.

It is more preferred that the length of the large diameter portion be relatively greater than the length of the small diameter portion.

It is more preferred that the rear locking member include a front small diameter portion having a front guide hole, which couples to the catheter, and a rear larger diameter portion having a rear guide hole extending a predetermined length from the front guide hole.

It is more preferred that the front guide hole be smaller than the inner diameter of the rear guide hole.

It is more preferred that a slope be provided between the front guide hole and the rear guide hole.

It is preferred that the cap member include a female thread portion for engaging with a male thread portion formed on the rear end of the rear guide hole and a sealing member for being inserted into the rear guide hole when the male and female thread portions are engaged with each other.

It is preferred that the cap member be connected to the rear locking member via a connector member having, a predetermined length.

According to the present invention, the front connector is connected to the guide tube into which the catheter is inserted, the adjustment tube is provided between the front and rear connectors, the front locking member is disposed inside the adjustment tube by being detachably assembled to the front connector, the rear locking member is detachably assembled to the rear connector by being connected to the rear end of the catheter, the cap member is detachably assembled to the rear locking member. With this configuration, it is possible to re-aspirate the body fluids or the blood clots, which remains in the operated area of the human body, by inserting the catheter through the guide tube, which is fixedly disposed such that part of the leading end is inserted into the human body, after the operation. Since the catheter can be moved forward and backward and be rotated, the leading end of the catheter can be precisely and simply located to an intended diseased area in the aseptic state. Accordingly, it is possible to simply, rapidly, and effectively remove remaining blood, rebleeding, and the abscesses from the diseased area of the patient on the bed by aspiration, thereby reducing the recovery period of the patient after the operation and preventing side effects of the operation.

BEST MODE

Figure 1:
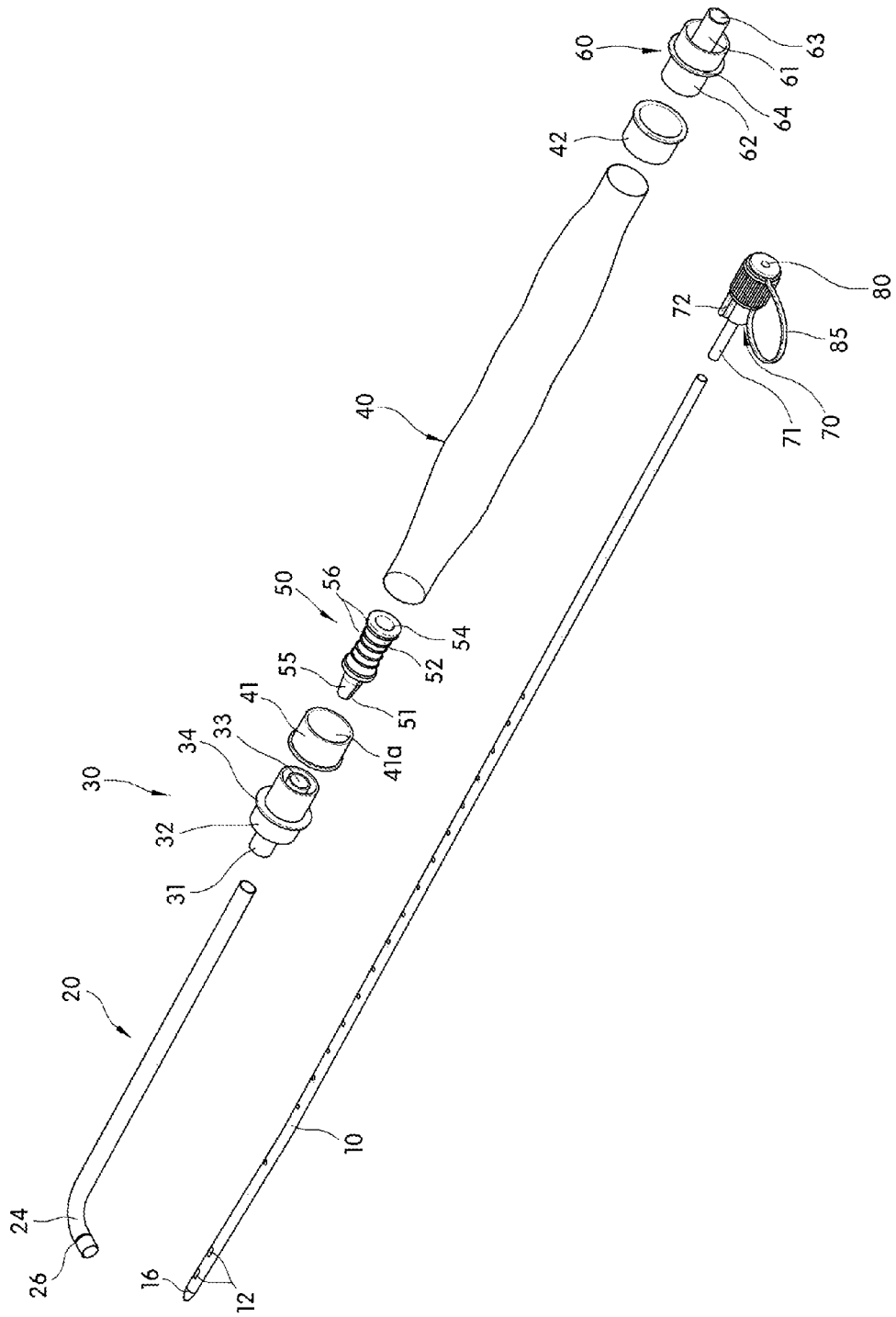
FIG. 1 is an exploded perspective view showing an aseptic re-aspiration catheter apparatus according to an exemplary embodiment of the invention.
Figure 2:
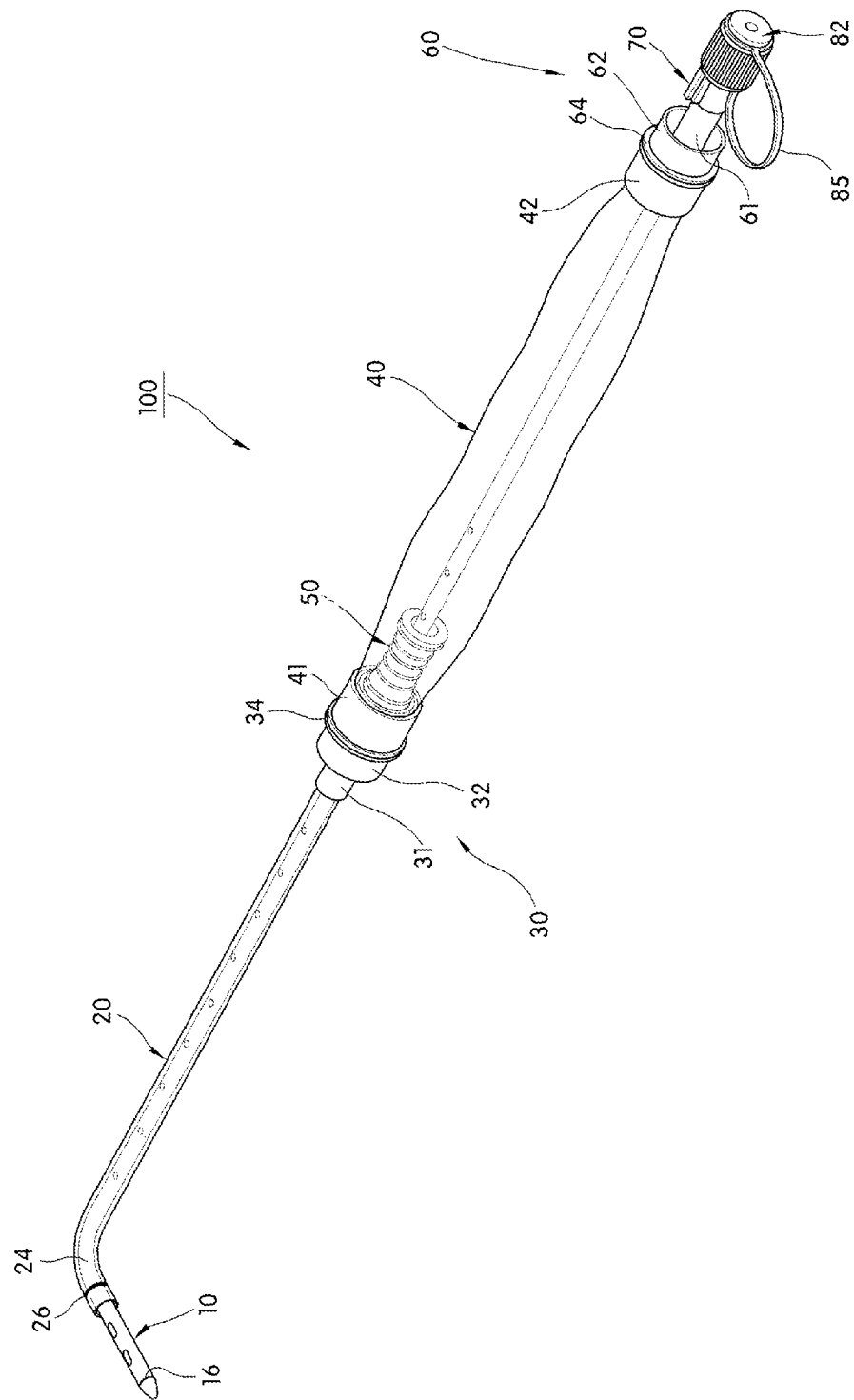
FIG. 2 is an overall perspective view showing the aseptic re-aspiration catheter apparatus according to an exemplary embodiment of the invention.

Hereinafter, exemplary embodiments of the invention will be described in more detail with reference to the accompanying drawings.

As shown in FIGS. 1 to 6, an exemplary embodiment of the invention provides an aspiration catheter 100, which is designed to remove substances by aspirating them from the human body. The aspiration catheter 100 includes a catheter 10, a guide tube 20, a front connector 30, an adjustment tube 40, a front locking member 5C, a rear connector 60, a rear locking member 70, and a cap member 80.

As shown in FIGS. 1 to 4, the catheter 10 is a hollow member having a predetermined length, which extends through the guide tube 20, the front and rear connectors 30 and 60, the front locking member 50, and the adjustment tube 40, such that the rear end thereof is connected to the rear locking member 70.

It is preferred that the catheter 10 be made of a resin material, such as silicone, to have flexibility such that it can be easily and freely flexed when inserted into the cranium or abdominal cavity.

In addition, it is preferred that the catheter 10 have a plurality of aspiration holes 12 penetrating the front end thereof such that body fluids can be aspirated when an aspiration force is provided.

As shown in FIGS. 1 to 4, the guide tube 20 is a tubular member having a predetermined length. The guide tube 20 has an inner hole 22 having an inner diameter the same as or greater than the outer diameter of the catheter 10, and is made of Teflon or the like.

The guide tube 20 has a burying portion 24 in the leading end thereof, the burying portion 24 being inclined at a predetermined angle, such that it can be disposed into the cranium or abdominal cavity, which is an area subjected to an operation, through the skin of the human body.

In addition, it is preferred that at least one ring- or line-shaped position locator 26 be provided in the leading end of the guide tube 20, in which the burying portion 24 is formed, such that the position inserted into the body can be more easily located. The position locator 26 is made of a material that does not allow radiation, such as x-rays, to easily pass through.

In addition, it is preferred that another position locator 16, which is the same as described above, be provided in the leading end of the catheter 10 such that the position of the leading end can be simply and precisely located when adjusting the position.

Accordingly, the position of the leading end of the guide tube 20, which is buried in the human body, and the position of the leading end of the catheter 10, which is buried in the human body through the guide tube 20, can be more easily and precisely located by the position locators 16 and 26.

Here, it is preferred that the position locators 16 and 26 be made of a material that is impenetrable by x-rays. The material may be one selected from among Au, Ag, Pt, Ta, Ir, W, and alloys thereof.

As shown in FIGS. 1 to 4, the front connector 30 is a connector member, which is connected to the rear end of the guide tube 20, through which the catheter 10 extends by being inserted thereinto.

The front connector 30 includes an inner tube 31, an outer tube 32, and a partition 34. The inner tube 31 has an inner hole 33 having a predetermined size such that the rear end of the guide tube 20 and the leading end of the front locking member 50 can be inserted into the inner hole 33. The outer tube 32 has an inner diameter relatively greater than that of the inner tube 31, and is assembled to the leading end of the adjustment tube 40. The partition 34 extends from the outer surface of the inner tube 31 such that it halves the space inside the outer tube 32.

Here, the partition 34 has at least one pore 34a, which penetrates the partition 34 such that the inside of the adjustment tube 40 communicates with the outside.

Accordingly, during the contraction and expansion of the adjustment 40, the pore 34a allows external air to be freely introduced into the adjustment tube 40 and air inside the adjustment tube 40 to be freely discharged to the outside. Thereby, the contraction and expansion of the adjustment tube 40 can be more efficiently performed.

In addition, the inner hole 33 has an inner diameter substantially the same as or smaller than the outer diameter of the guide tube 20 such that it is in contact with the outer surface of the guide tube 20.

It is preferred that the inner tube 31 be formed to be relatively longer than the outer tube 32. Although the leading and rear ends of the outer tube 32, divided by the partition 34, are shown as having different outer diameters, this is not intended to be limiting. Rather, the outer diameters of the leading and rear ends of the outer tube 32 can have the same size.

In addition, the partition 34 protrudes from the outer surface of the outer tube 32 such that it acts as a stopper when assembling a front sleeve 41, which will be described later.

As shown in FIGS. 1 to 4, the adjustment tube 40 is a tubular member having a predetermined length, with the leading end thereof being assembled to the rear end of the front connector 30, which is connected to the guide tube 20.

The adjustment tube 40 is made of a transparent or semi-transparent material such that the sate inside the tube can be easily identified from the outside. It is preferred that the adjustment tube 90 be made of an elastic material, such as urethane.

In addition, it is preferred that the adjustment tube 40 be made of a soft material, which can contract and expand along the long axis, such that the front locking member, which is disposed inside, can be manipulated in the long axis direction, with the position thereof being identified by eyes during the manipulation.

Here, according to the cross section of the adjustment tube 40, which is shown and described above, the outer diameter of the leading end, which is assembled to the front connector 30, increases in the backward direction, the outer diameter of the main portion extending in the longitudinal direction is constant, and the outer diameter of the rear end, which is assembled to the rear connector 42, decreases in the backward direction. However, this is not intended to be limiting, and the adjustment tube 40 can be provided as a bellows tube.

In addition, the leading end of the adjustment tube 40 is securely fixed in position by being in close contact between the inner surface of the front sleeve 41, which is inserted into the rear end of the outer tube 32 of the front connector 30, and the outer surface of the outer tube 32.

Here, it is preferred that the front sleeve 41 have a protrusion 41a formed on the inner surface thereof. When the front connector 30 and the adjustment tube 40 are assembled to each other, the protrusion 41a increases the fixing force with which the front connector 30 is brought into close contact with the outer diameter of the adjustment tube 40, so that the adjustment tube 40 is not easily dislodged after it is assembled.

As shown in FIGS. 1 to 4, the front locking member 50 has an inner hole into which the catheter 10, which has passed through the guide tube 20 and the front connector 30, is inserted. Thus, the front locking member 50 is moved forward and backward along with the adjustment tube 40, which is disposed inside the adjustment tube 40, so that the leading end thereof is inserted into or withdrawn from the inner hole 33 of the front connector 30.

The front locking member 50 includes a front body 51 and a rear body 52. The front body 51 has a front inner hole 53, into which the catheter 10 is inserted and fitted. Part of the leading end of the front body 51 is inserted into the inner hole 33 of the front connector 30. The rear body 52 extends from the front body 51, and has a rear inner hole 54, through which the catheter 10 extends. The leading end of the rear body 52 is in contact with the front connector 30.

Here, it is preferred that the front inner hole 53 have an inner diameter the same as or smaller than the outer diameter of the catheter 10 such that it contacts the outer surface of the catheter 10. It is preferred that the rear inner hole 53 extend from the front inner hole 53 and have an inner diameter greater than the outer diameter of the catheter 10 such that it does not contact the outer surface of the catheter 10.

Accordingly, when manipulating the catheter 10 via the front locking member 50 such that it moves forward and backward, it is possible to minimize the frictional force between the members, thereby improving the ease of manipulation.

In addition, the front body 51 has at least one slit 55, which is formed by cutting the leading end thereof in the longitudinal direction. In the front body 51, the outer diameter of the cross section increases in the direction toward the rear body 52.

Figure 3:
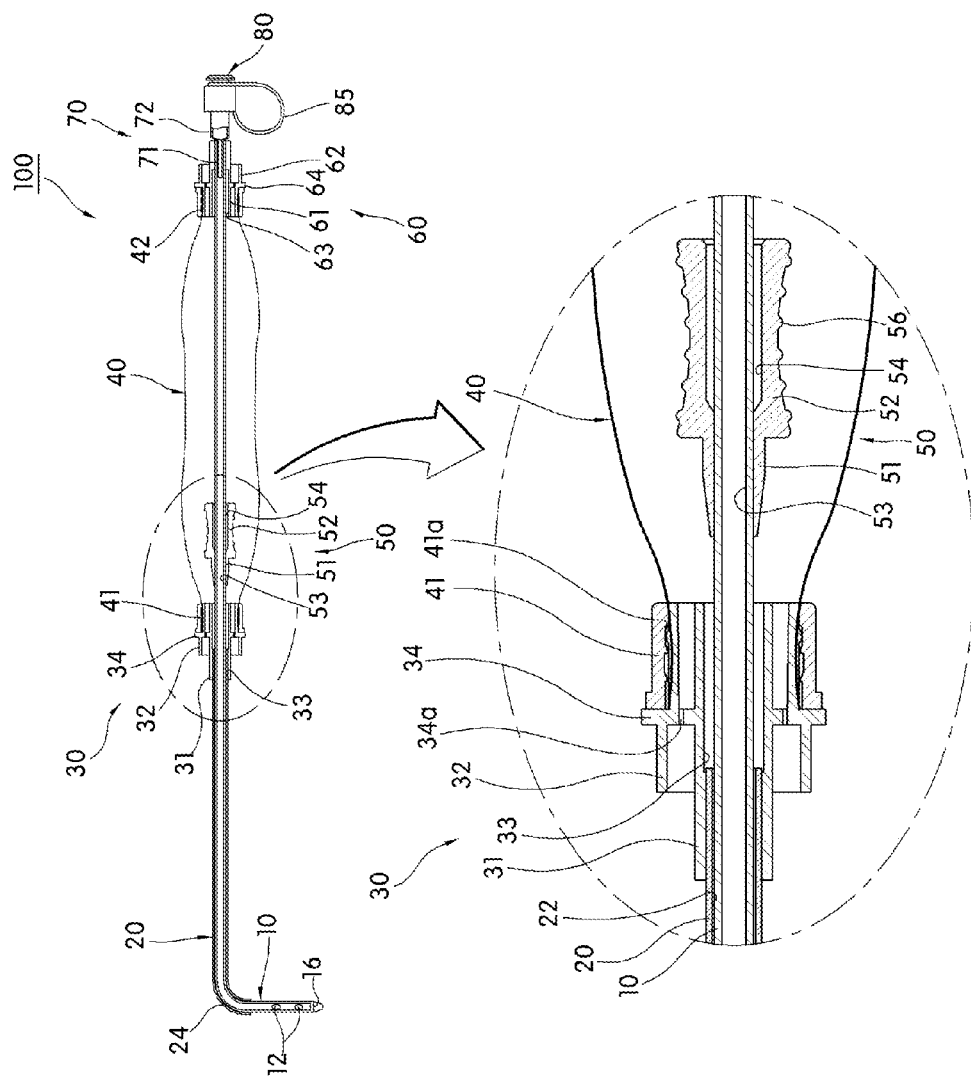
FIG. 3 is a configuration view showing the aseptic re-aspiration catheter apparatus according to an exemplary embodiment of the invention, in which the front locking member is fitted into the front connector.

Accordingly, when inserting the front body 51 of the front locking member 50 into the inner hole 33 of the front connector 30 as shown in FIG. 3, the front inner hole 53 of the front body 51 is naturally contracted by the slit 55, so that the outer surface of the catheter 10 inserted into the front inner hole 53 of the front body 51 is brought into contact with the inner surface of the front inner hole 53, thereby generating a frictional force. This as a result provides a locking function so that the catheter 10 does not easily move.

Figure 4:
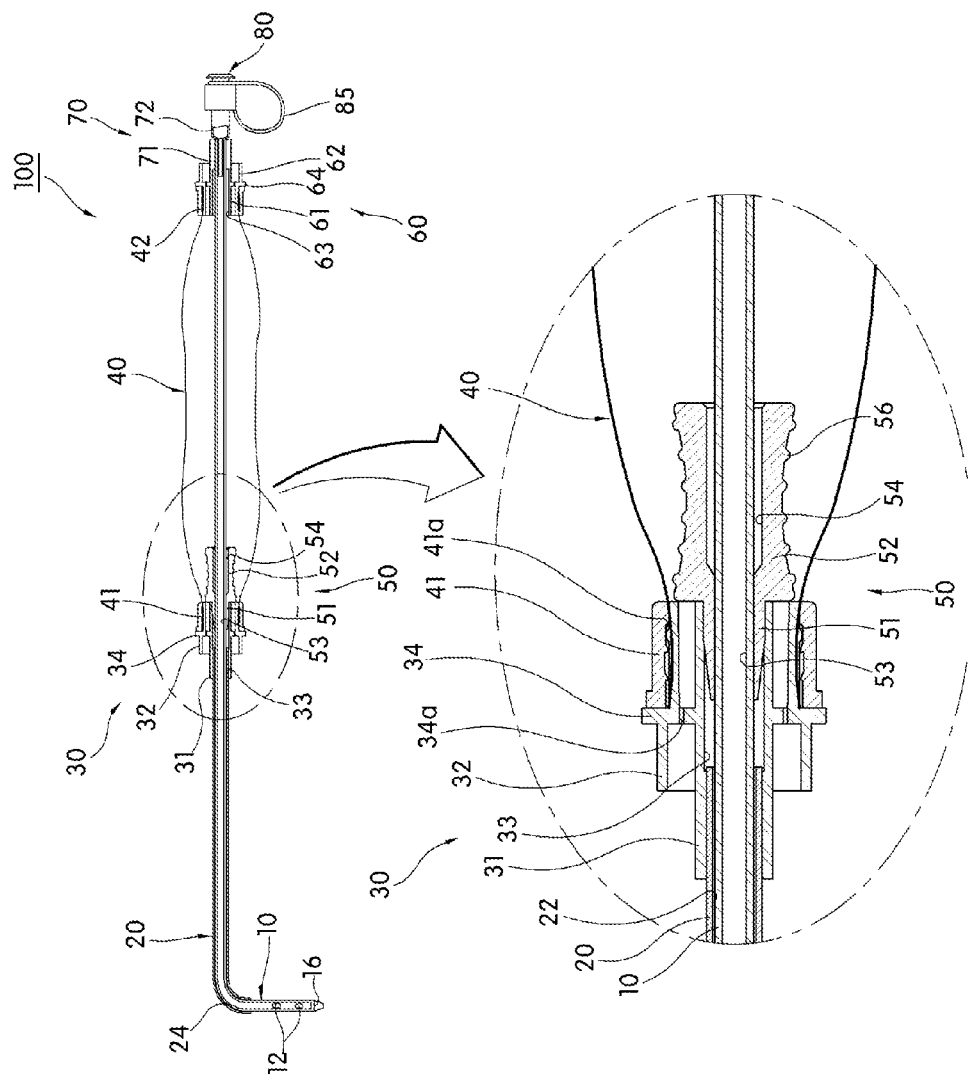
FIG. 4 is a configuration view showing the aseptic re-aspiration catheter apparatus according to an exemplary embodiment of the invention, in which the front locking member is separated from the front connector.
Figure 5:
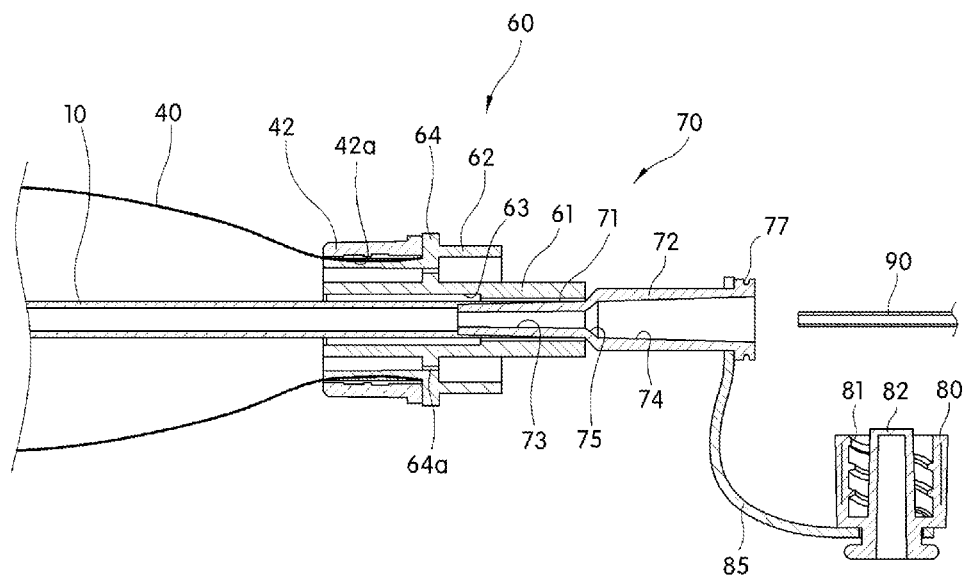
FIG. 5 is a configuration view showing the aseptic re-aspiration catheter apparatus according to an exemplary embodiment of the invention, in which the rear locking member is fitted into the rear connector.
Figure 6:
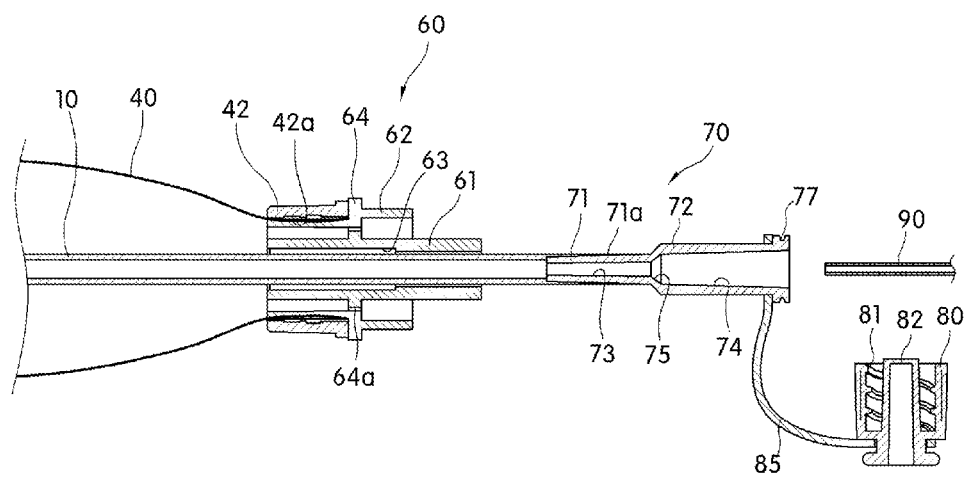
FIG. 6 is a configuration view showing the aseptic re-aspiration catheter apparatus according to an exemplary embodiment of the invention, in which the rear locking member is separated from the rear connector.

In contrast, when detaching the front body 51 of the front locking member 50 from the inner hole 33 by moving it backward from the front connector 30 as shown in FIG. 4, the front inner hole 53 of the front body 51 is naturally expanded by the slit 55, so that the outer surface of the catheter 10 inserted into the front inner hole 53 of the front body 53 is detached from the inner surface of the inner hole 53 or the contacting force between the outer surface of the catheter 10 and the inner surface of the inner hole 53 is removed. This as a result disables the locking function so that the catheter 10 can move. Accordingly, it is possible to freely vary the position of the leading end of the catheter 10 by moving the catheter 10 forward and backward through the guide tube 20.

In addition, it is preferred that the size of the rear body 52 be greater than the inner diameter of the outer tube 32, which is provided on the rear end of the front connector 30, and smaller than the outer diameter of the outer tube 32.

This can prevent air from being introduced through the pore 34a by closing the inlet end between the inner tube 31 and the outer tube 32 of the front connector 30 when inserting the front body 51 into the inner hole 33 of the front connector 30. Thereby, it is possible to fundamentally prevent external air from being introduced into the adjustment tube 40 through the pore 34a when locking the catheter 10.

In addition, the rear body 52 is provided with a cross sectional shape, in which the outer diameter of the central portion is relatively smaller than those of the opposite ends, such that a plurality of protrusions 56 is formed on the outer surface thereof or a curved cross section, which is concaved downward, is formed. Accordingly, when manipulating the front locking member 50, the user can easily grab it and be prevented from slipping.

As shown in FIGS. 1, 2, 3, and 6, the rear connector 60 is a connector member, through which the catheter 10 extends by being inserted thereinto. The rear connector 60 is connected to the rear end of the adjustment tube 40, and is connected to the leading end of the rear locking member 70.

The rear connector 60 is provided such that it has a shape substantially the same as that of the front connector 30. The rear connector 60 includes an inner tube 61, an outer tube 62, and a partition 64. The inner tube 61 has an inner hole 63 having a predetermined size such that the catheter 10 is moved forward and backward through the inner tube 61 by being inserted thereinto. The outer tube 62 has an inner diameter relatively greater than that of the inner tube 61, and is assembled to the rear end of the adjustment tube 40. The partition 64 extends from the outer surface of the inner tube 61 such that it halves the space inside the outer tube 62.

Here, the partition 64 has at least one pore 64a, which penetrates the partition 64 such that the inside of the adjustment tube 40 communicates with the outside.

Accordingly, during the contraction and expansion of the adjustment 40, the pore 64a allows external air to be freely introduced into the adjustment tube 40 and air inside the adjustment tube 40 to be freely discharged to the outside. Thereby, the pore 64a together with the pore 34a of the front connector 30 can help the adjustment tube 40 be more efficiently contacted and expanded.

In addition, the inner hole 63 may include a large diameter portion and a small diameter portion. The large diameter portion has an inner diameter relatively greater than the outer diameter of the catheter 10, which extends therethrough, such that it is spaced apart from the outer surface of the catheter. The small diameter portion has an inner diameter relatively the same as the outer diameter of the catheter 10, such that it contacts the outer surface of the catheter.

Here, it is preferred that the length of the large diameter portion be formed relatively greater than the length of the small diameter portion in order to minimize the frictional force that is generated during the forward/backward movement of the catheter 10, so that the operation of adjusting the position of the catheter can be more efficiently performed.

It is preferred that the inner tube 61 be longer than the outer tube 62. Although the outer tube 62 has been shown and described as the front and rear ends on both sides of the partition 64 have different outer diameters, this is not intended to be limiting. Rather, the front and rear ends can be formed with the same size.

In addition, the partition 64 protrudes from the outer surface of the outer tube 62 such that it acts as a stopper when assembling a rear sleeve 42, which will be described later.

In addition, the rear end of the adjustment tube 40 is securely fixed in position by being brought into close contact between the inner surface of the rear sleeve 42, which is inserted into the leading end of the outer tube 62 of the rear connector 60, and the outer tube 62.

Here, it is preferred that the rear sleeve 42 also have a protrusion 42a formed on the inner surface thereof. When assembling the rear connector 40 and the adjustment tube 40 to each other, the protrusion 42a increases the fixing force with which the rear connector 40 is brought into close contact with the outer diameter of the adjustment tube 40, so that the adjustment tube 40 is not easily dislodged after it is assembled.

As shown in FIGS. 1, 2, 5, 6, the rear locking member 70 is a locking member, which is connected to the rear end of the catheter 10 extending through the guide tube 20, the front and rear connectors 30 and 60, the front locking member 50, and the adjustment tube 40, and is inserted into or detached from the inner hole 63 of the rear connector 60.

The rear locking member 70 includes a front small diameter portion 71 and a rear large diameter portion 72. The front small diameter portion 71 has a front guide hole 73 having a predetermined size, and is coupled to or decoupled from the rear connector 60, such that the leading end thereof is coupled to the catheter 10 by being inserted into the inner hole thereof. The rear large diameter portion 72 has a rear guide hole 74 extending backward a predetermined length from the front guide hole 73, has an outer diameter relatively greater than that of the front small diameter portion 71, and is coupled to the rear end of the rear connector 60.

Accordingly, the inner hole of the catheter 10 communicates with the front and rear guide holes 73 and 74 of the rear locking member 70, such that the aspiration force transmitted to the rear locking member is transmitted up to the catheter 10. Thereby, the aspiration force generated from the aspiration hole, which is formed in the leading end of the catheter 10, can remove blood fluids, blood clots, abscesses, and the like from the human body by discharging them to the outside.

Here, it is preferred that the front guide tube 73 be formed smaller than the inner diameter of the rear guide tube 63, and that a slope 75 be formed in the boundary area between the front guide hole 73 and the rear guide hole 74, so that the needle of a syringe 90, which provides the aspiration force, can be easily inserted.

In addition, a protrusion 71a can be formed on the outer surface of the small diameter portion 71 in order to further enhance the contacting force between the outer surface of the small diameter portion 71 and the inner surface of the catheter 10 when connecting the small diameter portion 71 to the catheter 10.

As shown in FIGS. 1, 2, 5, and 6, the cap member 80 is a sealing member, which is detachably coupled to the rear locking member 75 in order to selectively close the inlet end, i.e. the rear end, of the rear guide tube 74.

The cap member 80 includes a female threat portion 81 and a sealing member 82. The female thread portion 81 is formed to engage with a male thread portion 77, which is formed on the inlet end, i.e. the rear end, of the rear guide tube 74. The sealing member 82 is inserted into the rear guide hole 74 when the male and female thread portions come into engagement with each other.

Here, the sealing member 82 can be provided in the form of a cylinder that has an outer diameter substantially the same as the inner diameter of the rear guide hole 74 such that it comes into close contact with the inner surface of the rear guide hole 74.

In addition, it is preferred that the cap member 80 be connected to the rear locking member 70 via the connector member 85 having a predetermined length in order to prevent the cap member 80 from being lost when decoupling the male and female thread portions from each other.

The catheter apparatus 100 having the above-described configuration according to an exemplary embodiment of the invention is used when bleeding, abscesses, blood clots, or the like have occurred in the cranium or abdominal cavity. This ensures that the burying portion 24, i.e. the leading end, of the guide tube 20 remains inside the body through an operation, and thus discharges the body fluids or abscesses from the body to the outside by aspirating them during the operation. The catheter apparatus 100 is not removed right after the operation. The operation is finished in the state in which the catheter apparatus 100 is fixed in the inserted position.

In the meantime, when a great amount of blood that has bled remains in the human body or the amount of bleeding increases even after an operation for the cranium or abdominal cavity, a reoperation is required. However, using the catheter apparatus of the invention, which is previously installed, can safely and simply remove the body fluids or abscesses by aspirating them in the aseptic state.

That is, the catheter 1C having a predetermined length is inserted into the guide tube 20, the front connector 30 is assembled to the rear end of the guide tube 20, the adjustment tube 40 having a predetermined length is assembled between the front connector 30 and the rear connector 60, the front locking member 50 is assembled inside the adjustment tube 40, the rear locking member 70 is assembled to the rear connector 60, and the cap member 80 is assembled to the rear locking member 70.

Here, in the catheter 10 inserted through the guide tube 20, the leading end is located inside the human body, and the rear end is connected to the front and rear guide holes 73 and 74 of the rear locking member 70.

In this state, when the cap member 80, which is screw-engaged with the rear body 72 of the rear locking member, is disengaged, the rear guide hole 79 of the rear locking member 70 is exposed to the outside.

Afterwards, the leading end of the aspirating syringe 90 is inserted through the rear guide hole 74 to the front guide tube 73, and then an aspiration force is provided to the catheter 10 using the aspirating syringe 90. The provided aspiration force is transmitted to the aspiration hole 12, which is formed in the leading end of the catheter 10, so that body fluids or abscesses can be simply and easily discharged from the human body by being forcibly aspirated through the catheter.

In the meantime, in the case of intending to reposition the aspiration area of the catheter, the front locking member 50 is grabbed and pulled backward by the hand, which has been holding the adjustment tube 40. Then, the locking member 50, which has been assembled to the front connector 30, is separated as shown in FIG. 4.

In this case, the front inner hole 53 of the front body 51, into which the catheter 10 is inserted, is naturally expanded by the slit 55, so that the contacting force between the outer surface of the catheter 10 and the inner surface of the front inner hole 53 is removed. This as a result makes it possible to move the catheter 10 forward or backward through the guide tube 20, thereby simply repositioning the aspiration area, which is the leading end of the catheter 10.

In subsequence, after the operation of repositioning the re-aspiration area of the catheter is finished, the front locking member 50 is grabbed and pushed forward by the hand, which has been holding the adjustment tube 40. Then, the locking member 50, which has been separated from the connector 30, is reassembled to the front connector 30 as shown in FIG. 3.

In this case, the front inner hole 53 of the front body 51 is naturally contracted by the slit 55, thereby generating a contacting force between the outer surface of the catheter 10 and the inner surface of the front inner hole 53. This as a result converts the apparatus into a locking state so that the catheter 10 does not easily move.

During the contraction and expansion of the adjustment tube, which the user grabs in the operation of adjusting the catheter, air remaining in the space inside the adjustment tube is naturally discharged to the outside or external air is naturally introduced into the space inside the adjustment tube through the pores 34a and 64a of the partitions 34 and 64 of the front and rear connectors 30 and 60, so that the contraction/expansion of the adjustment tube 40 can be efficiently performed.

In addition, with the leading end of the catheter 10 and the leading end of the guide tube 20, it is possible to more simply and precisely locate the aspiration position of the catheter, which is inserted into the human body, and the burying position of the guide tube.

While the present invention has been shown and described with reference to the certain exemplary embodiments thereof, it will be understood by those skilled in the art that various changes in form and details may be made therein without departing from the spirit and scope of the present invention as defined by the appended claims and their equivalents.

The invention claimed is:

1. An aseptic re-aspiration catheter apparatus for removing body fluids from a human body, comprising:
   a front connector connected to a guide tube, into which a catheter having a predetermined length is inserted;
   an adjustment tube having a predetermined length, a front end of the adjustment tube being assembled to the front connector;
   a front locking member having an inner hole into which the catheter is inserted, wherein the front locking member is detachably assembled to the front connector and is disposed inside the adjustment tube;
   a rear connector assembled to a rear end of the adjustment tube;
   a rear locking member connected to the catheter and detachably assembled to the rear connector, wherein the catheter extends through the front and rear connectors; and
   a cap member detachably assembled to the rear locking member;
   wherein the front end of the adjustment tube is fixed in position by a front sleeve, wherein the front sleeve is inserted into a rear end of the front connector, and the rear end of the adjustment tube is fixed in position by a rear sleeve, wherein the rear sleeve is inserted into a front end of the rear connector, wherein the front connector includes:
- an inner tube having an inner hole such that a rear end of the guide tube and a leading end of the front locking member are inserted into the hole;
- an outer tube having an inner diameter greater than that of the inner tube, wherein the outer tube is assembled to the leading end of the adjustment tube; and
- a partition extending from an outer surface of the inner tube such that the partition divides a space inside the outer tube, wherein the partition has at least one pore, wherein the pore penetrates the partition such that a space inside the adjustment tube communicates with an outside.

2. The aseptic re-aspiration catheter apparatus according to claim 1, wherein the catheter has a plurality of aspiration holes in a leading end thereof.

3. The aseptic re-aspiration catheter apparatus according to claim 1, wherein the guide tube has a burying portion on a leading end thereof, the burying portion inclined at a predetermined angle.

4. The aseptic re-aspiration catheter apparatus according to claim 1, wherein the catheter or the guide tube has at least one position locator made of a material that prevents radiation from passing through.

5. The aseptic re-aspiration catheter apparatus according to claim 1, wherein the adjustment tube is made of a material, which is transparent or semitransparent such that an inside of the adjustment tube is identifiable by eyes, and is soft such that the adjustment tube is contractible and expandable along a long axis.

6. The aseptic re-aspiration catheter apparatus according to claim 1, wherein the front locking member includes a front body having a front inner hole into which the catheter is inserted and fitted, with part of a leading end of the front body being inserted into an inner hole of the front connector, and a rear body extending from the front body, wherein the rear body has a rear inner hole through which the catheter extends, and a leading end of the rear body is in contact with the front connector.

7. The aseptic re-aspiration catheter apparatus according to claim 6, wherein the front inner hole has an inner diameter equal with or smaller than an outer diameter of the catheter, and the rear inner hole has an inner diameter greater than the outer diameter of the catheter.

8. The aseptic re-aspiration catheter apparatus according to claim 6, wherein the front body has at least one slit in a leading end thereof, the leading end having a cross section such that an outer diameter thereof increases in a direction toward the rear body.

9. The aseptic re-aspiration catheter apparatus according to claim 6, wherein the rear body has a size greater than an inner diameter of an outer tube, which is provided on a rear end of the front connector, and smaller than an outer diameter of the outer tube.

10. The aseptic re-aspiration catheter apparatus according to claim 6, wherein the rear body has a plurality of protrusions formed on an outer surface thereof.

11. The aseptic re-aspiration catheter apparatus according to claim 6, wherein the rear body has a cross section such that an outer diameter of a central portion thereof is relatively smaller than those of opposite ends thereof.

12. The aseptic re-aspiration catheter apparatus according to claim 1, wherein the rear connector includes an inner tube having a predetermined size through which the catheter is moved forward and backward by being inserted thereinto, an outer tube having an inner diameter relatively greater than the inner tube, the outer tube assembled to the rear end of the adjustment tube, and a partition extending from an outer surface of the inner tube to divide a space inside the outer tube.

13. The aseptic re-aspiration catheter apparatus according to claim 12, wherein the partition has at least one pore, the pore penetrating the partition such that a space inside the adjustment tube communicates with an outside.

14. The aseptic re-aspiration catheter apparatus according to claim 12, wherein the inner hole includes a large diameter portion spaced apart from an outer surface of the catheter, the large diameter portion having an inner diameter relatively greater than an outer diameter of the catheter, and a small diameter portion contacting the outer surface of the catheter.

15. The aseptic re-aspiration catheter apparatus according to claim 14, wherein a length of the large diameter portion is relatively greater than a length of the small diameter portion.

16. The aseptic re-aspiration catheter apparatus according to claim 1, wherein the rear locking member includes a front small diameter portion having a front guide hole, which couples to the catheter, and a rear large diameter portion having a rear guide hole extending a predetermined length from the front guide hole.

17. The aseptic re-aspiration catheter apparatus according to claim 16, wherein the front guide hole is smaller than an inner diameter of the rear guide hole.

18. The aseptic re-aspiration catheter apparatus according to claim 16, wherein a slope is provided between the front guide hole and the rear guide hole.

19. The aseptic re-aspiration catheter apparatus according to claim 16, wherein the cap member includes a female thread portion for engaging with a male thread portion formed on a rear end of the rear guide hole and a sealing member for being inserted into the rear guide hole when the male and female thread portions are engaged with each other.

20. The aseptic re-aspiration catheter apparatus according to claim 1, wherein the cap member is connected to the rear locking member via a connector member having a predetermined length.

* * * * *